United States Patent [19]
Kayser

[11] Patent Number: 6,069,012
[45] Date of Patent: May 30, 2000

[54] VERSATILE FLUIDIZED BED REACTOR

[75] Inventor: John C. Kayser, Houston, Tex.

[73] Assignee: Kayser Technology, Inc., Houston, Tex.

[21] Appl. No.: 08/862,657

[22] Filed: May 23, 1997

[51] Int. Cl.$^7$ .............................. G01N 31/10; B01J 8/18
[52] U.S. Cl. .......................... 436/37; 422/130; 422/139; 422/145
[58] Field of Search .................................... 422/130, 139, 422/145, 140, 146; 436/37

[56] References Cited

U.S. PATENT DOCUMENTS

| | | | |
|---|---|---|---|
| 2,684,987 | 7/1954 | Mantell et al. | 260/653 |
| 4,556,537 | 12/1985 | Honma | 422/130 |
| 4,702,888 | 10/1987 | Borgialli | 422/130 |
| 4,923,593 | 5/1990 | Marcilly et al. | 208/113 |
| 5,186,904 | 2/1993 | Lyzinski et al. | 422/130 |
| 5,262,104 | 11/1993 | Schwartz | 264/81 |
| 5,501,789 | 3/1996 | Bartholic | 208/146 |

OTHER PUBLICATIONS

Handbook of Petroleum Refining Processes (Chemical Process Technology Handbook Series) R. Meyers, McGraw–Hill, 1986, pp. 111–117.

Brochure entitled, UOP Fluid Catalytic Cracking Process, P. A. Tajbl, 2–10, 225.

*Primary Examiner*—Hien Tran
*Attorney, Agent, or Firm*—Winstead Sechrest & Minick P.C.; Dwayne L. Mason

[57] ABSTRACT

A laboratory scale fluid catalytic cracking apparatus and method of use thereof, which provides cracking performance that emulates commercial riser cracking. The apparatus includes a reactor having a removable feed injector to quickly facilitate changing hydrocarbon contact time without varying the feed rate or diluent rates, or catalyst charge, and also without the expense of a new reactor. The feed injector is a tube within a tube design. The feed injector allows hydrocarbon feed as well as fluidization gas to be delivered to a prescribed axial position within a catalyst bed in the reactor to directly affect hydrocarbon contact time. The reactor also includes a conical bottom head having a conical section and a lower fluidization gas nozzle connected at its apex. The total included angle of the conical section may vary between 10° and 1700°, however it is preferred to be in the range of The reactor geometry combined with the location of the fluid and gas sources generate the desired torroidal motion of the catalyst bed, which is significantly enhanced over conventional designs which do not use multiple nozzles and the conical bottom design.

15 Claims, 7 Drawing Sheets

FIGURE 1

VERSATILE FLUIDIZED BED REACTOR

TECHNICAL FIELD

The present invention relates to the design of a fluidized bed reactor one use of which is for laboratory evaluation of the fluid catalytic cracking process with particular regard to catalysts, feedstocks, and process parameters. Fluid catalytic cracking is the dominant catalytic process for producing transportation fuels and chemical feedstocks worldwide. Consequently, extensive efforts have been made at developing useful laboratory tests pertinent to this process for the purposes of developing improved catalysts, quantifying and correlating the cracking character of various feedstocks based on their respective properties, understanding the implications of different process conditions, and improving commercial process design. The present invention also relates to the design of fluidized bed reactors, which have applications in the hydrocarbon and chemical process industries on both commercial and laboratory scales.

BACKGROUND

The two broad approaches commonly used in the laboratory for studying the fluid catalytic cracking process are continuous processing units and batch processing units. The continuous processing units are basically scaled-down versions of commercial operating units and are typically very complex systems that are expensive to construct, operate, and maintain. In addition, they require large samples of catalyst as well as feed compared to batch laboratory cracking units. Batch processing units use a single charge of catalyst (typically less than 200 gms.) and process a small sample mass of feed that is usually injected over the catalyst for a period of time on the order of a minute. The ratio of the catalyst mass to the feed mass is referred to as the catalyst-to-oil ratio and typically ranges from 3 to 10. Batch processes provide considerable cost and speed advantages over continuous units for laboratory studies, primarily because of their relative simplicity and the smaller scale.

Two types of batch processes are commonly used: fixed bed and fluidized bed. Fixed bed type units are not appropriate for processing high boiling range feeds, which are often the feed for commercial fluid catalytic cracking units (FCCU). For this and other reasons, many laboratories have abandoned the use of fixed bed reactors for evaluating commercial FCCU operation. Thus, fluidized bed reactors are preferred over fixed bed reactors for studying the fluid catalytic cracking process on a laboratory scale.

One of the most important parameters in fluid catalytic cracking is the time that hydrocarbons are in contact with catalyst. Research over the past several years uncovered that as much as 90% of the feed conversion takes place in the short contact time condition in the feed and catalyst mix-zone of the riser reactor in commercial FCCUs. This knowledge led to the revamp of older and larger reactors to smaller designs, because contact time dramatically affects yields and performance. Normally, reducing the contact time requires that the commercial unit operate at a higher catalyst-to-oil ratio than when the contact time is longer. It is therefore important for laboratory scale fluidized catalytic cracking apparatus to provide the flexibility to vary contact time and simultaneously operate at high catalyst-to-oil ratios.

There are several ways to vary contact time in laboratory fluid-bed reactors. The widely known techniques of altering the hydrocarbon feed rate, the rates of any diluent gases, and/or altering the catalyst charge provide results, however, they are not entirely consistent with commercial experience or have other deficiencies which limit their applicability.

Walsh, U.S. Pat. No. 4,419,328, discloses a laboratory apparatus for investigating the performance of catalytic cracking catalyst utilizing batch techniques and a fluidized bed reactor. Walsh teaches the use of the laboratory apparatus and techniques for obtaining cracking data but not a reactor apparatus or method that can be utilized to emulate the performance characteristics expected in a commercial scale reactor. Walsh discloses a fluidized bed reactor but it does not include a movable feed injector or disclose in any way the important aspects pertaining to injector location and its relationship to controlling hydrocarbon contact time. Walsh does not disclose or teach the injection of multiple feeds at different locations. In addition, Walsh does not disclose or teach an apparatus or method to achieve the catalyst circulation pattern within the reactor including its relation to commercial catalytic cracking as well as ways to enhance the circulation by proper reactor design and injector positioning.

It is well known that fluidized bed reactors of many different designs often exhibit a preferred flow of solids up the center core and return of solids down the normally cylindrical containing wall. Perry's Chemical Engineers' Handbook (Copyright 1984) mentions this tendency (Section 20 pg. 66) and the effect is noted in U.S. Pat. No. 5,262,104-Schwartz. In these references, however, there is no recognition of the potential applications of the circulation pattern nor are any ways to enhance the circulation provided.

SUMMARY

The present invention provides a method and apparatus for contacting hydrocarbon feed and catalyst in a laboratory or commercial scale fluidized bed and also controlling the time the hydrocarbons are in contact with the catalyst. More specifically, the axial position of the feed injector may be accurately positioned to vary the distance traveled by reactant and product hydrocarbons before they exit the catalyst bed. The closer the feed point is to the top or exit of the fluid bed the shorter the contact time between hydrocarbon and catalyst. This technique offers several advantages over the other known methods for varying contact time: altering the hydrocarbon feed rate, diluent rates, and/or the catalyst mass.

If the feed rate is increased to reduce the hydrocarbon contact time then the catalyst circulation pattern changes in an uncontrollable way as does the contacting of the feed and catalyst. In addition, at constant catalyst-to-oil ratio, varying the feed injection rate requires changing the injection time, which adds complication to the kinetic analysis and comparison of the results with commercial scale FCCUs. The present invention shows that moving the feed injector does not significantly alter the catalyst fluidization pattern, as compared with altering the feed rate, and does not require any changes in the injection time to attain a prescribed catalyst-to-oil ratio.

Varying the diluent rates has the same effect on catalyst patterns as changing the feed rate. In addition, varying diluent rates changes the hydrocarbon partial pressure which affects yields and performance. Simply moving the feed injector does not affect hydrocarbon partial pressure.

Decreasing the catalyst load to decrease contact time reduces bed height and can result in a short bed within which it is more difficult to distribute the hydrocarbon feed and produces more erratic yields. In addition, as catalyst load is reduced it becomes difficult to measure yields at high catalyst-to-oil ratio which is inherently important to reduced contact time operation. This difficulty is because the feed mass is very low and difficult to account for in a mass balance (at high catalyst-to-oil ratio with reduced catalyst mass). In addition, at constant catalyst-to-oil ratio, varying the catalyst load to affect contact time also requires changing the feed injection time, which adds complication to the kinetic analysis and comparison of results with commercial scale FCCUs.

Another feature of the invention couples the reactor geometry with the gas and feed supply rates and injector locations to provide enhanced catalyst circulation up the center core of the reactor and down the walls. This pattern is natural to fluidized beds, but it is enhanced by the present invention and such enhancement improves the performance so as to closely replicate that of a commercial scale FCCU. The conical bottom eliminates catalyst dead zones or regions of poor circulation and the feed injector supplies feed directly onto the catalyst. The catalyst circulation provides a high local ratio of catalyst-to-feed at the tip of the feed injectors at any point in time. This results in a more complete utilization of the catalyst. The enhanced catalyst circulation also provides for improved heat transfer to and from the catalyst and reactor contents at the wall surface of the reactor. Many applications may benefit from improved heat transfer.

One objective of the present invention is to provide a laboratory reactor design for evaluating the fluid catalytic cracking process that yields results that are comparable to commercial operations including a method for studying the effects of varying the hydrocarbon contact time.

Another objective of the present invention is to provide a reactor design geometry that yields a highly coherent catalyst circulation pattern, which is well suited for providing a performance closer to that of an ideal plug flow reactor rather than a continuous stirred tank reactor with respect to both the contacting of hydrocarbon and catalyst, and the conversion of the feed materials to products. This aspect of the present invention enables it to be utilized in many applications in the hydrocarbon processing and chemical processing industries. The fluidized bed resulting from the present invention has considerably more stability, more repeatable hydrodynamics, and more efficient catalyst utilization. These enhancements provide more precise and relevant performance over a wider range of velocity and may allow for higher feed throughput without degradation in performance.

Another objective of the present invention is to provide a versatile fluidized bed reactor that emulates the yield performance of commercial fluid catalytic cracking units, which inject feed to be cracked at one or more feed locations in a nearly ideal plug flow riser reactor. Heretofore, either different equipment or a totally new reactor was necessary to accomplish the desired testing in the laboratory. Multiple feed locations are necessary since different feeds require different contact times to obtain optimal yields. The present invention accomplishes this in that contact time may be varied by the methods described herein utilizing the reactor of the present invention without modification to accommodate multiple feeds while producing commercially relevant results.

Another objective of the present invention is to provide a reactor design, which may be used in processes other than fluid catalytic cracking. For example, the methods and apparatus described herein may be used in catalyst deactivation of fluid catalytic cracking catalyst as well as for chemical reactions including but not limited to partial oxidation reactions, an example of which is oxidation of ethylene to produce ethylene oxide.

DETAILED DESCRIPTION OF THE INVENTION

Figure 1:
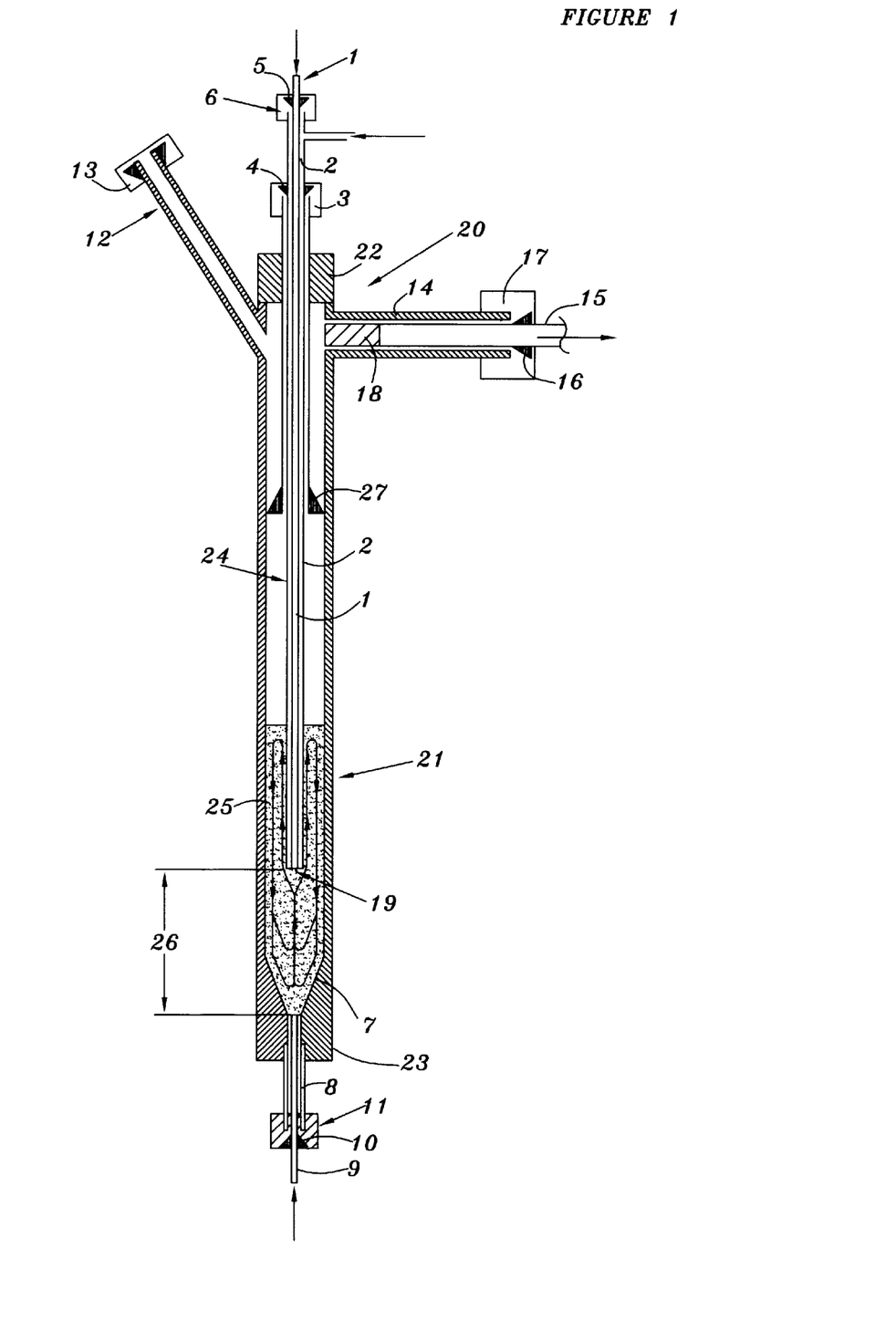
FIG. 1 is a schematic representation of a fluidized bed reactor.

FIG. 1 is a schematic representation of a fluidized bed reactor of the present invention. The fluidized bed reactor 20 shown in FIG. 1 comprises a reactor shell 21 having a top head 22 and a bottom head 23 connected at either end of the shell forming a pressure vessel.

A feed injector 24 is shown extending from above the reactor top head 22 axially through the top head 22 and into the interior of the reactor 20, and a catalyst bed 25. The preferred embodiment of the feed injector 24 is a tube within a tube configuration as illustrated in FIG. 1. The inner tube of the feed injector 24 includes a hydrocarbon and carrier gas feed line 1, which extends axially through an upper fluidization gas line 2 comprising the outer tube of the feed injector 24. While the feed injector 24 is shown extending through the reactor top head 22, it may be positioned at any location so as to allow the feed injection point to be located at any point within the catalyst bed 25. The feed injector 24 is removably connected to the reactor top head 22 via injector coupling 3. The injector coupling 3 (as well as the feed line coupling 6 and bottom head coupling 11 discussed below) comprises a SWAGELOK® or similar type fitting means. A compression fitting 4 or similar means is disposed about the exterior of the fluidization gas line 2 to seal against a seat within the reactor top head 22 such that when the injector coupling 3 is connected to the reactor top head 22 a pressure tight seal is formed. One who is skilled in the art will understand the injection point, designated by upper arrow 26, of the fluidization gas as well as the hydrocarbon feed and carrier gas within the catalyst bed 25 is determined by the length of tubing comprising the injector 24, which extends below the compression fitting 4 seated within the reactor top head 22. Therefore, to change the injection point within the catalyst bed 25, the injector coupling 3 is simply removed from the reactor top head 22, the respective feed injector is removed and a new injector of a prescribed length is installed in its place. The feed line 1 similarly has a compression fitting 5 disposed about the exterior of the feed line 1 and seals against a seat within the upper end of the fluidization gas line 2. The feed line 1 is removably retained by feed line coupling 6 together with the compression fitting 5 forming a pressure tight seal. While the outlet or injection point of both the feed line 1 and the fluidization gas line 2 as shown in FIG. 1 terminate at the same point within a catalyst bed 25, it is within the scope of the present invention that each may be terminated at different points within the catalyst bed 25. The feed injector 24 and fluidization gas line 2 are used to supply inert gas, such as nitrogen or steam, to the feed injection point, upper arrow 26, to both prevent catalyst particles from entering and plugging the feed line 1 and to cool the injector. The feed injector 24 of FIG. 1 is shown as a tube within a tube directed downward into the interior catalyst bed 25 of the reactor 20. However, the feed injector 24 may as noted above, be connected through the bottom aiming vertically upward. An injector centering means 27 may be connected directly to the bottom surface of the reactor top head 22 or to the reactor shell 21. The centering means 27 provides a guide path for the feed injector 24 so that the injector 24 remains aligned with the axis of reactor 20.

The bottom head 23 includes a conical section 7 of the reactor 20. The bottom head 23 also includes a fluidization nozzle 8, connected at the bottom or apex of the conical section 7, through which a lower fluidization gas line 9 extends upward to provide fluidization gas, such as nitrogen or other diluent, to the catalyst bed 25, and if desired serves as an alternate source for feed injection. The total included angle of the conical section 7 designated as θ may vary from 10° to 170°, but in the preferred embodiment the total included angle of the conical section is in the range of 20° to 60°. The fluidization gas line 9 extends through the interior of the fluidization nozzle 8 and terminates approximately at the apex of conical section 7. As similarly described above, a compression fitting 10 is disposed about the exterior of the fluidization line 9 to sealingly engage with a seat within the fluidization nozzle 8. A fluidization coupling or bottom head coupling 11 is removably connected to the fluidization nozzle 8 to provide a pressure tight seal between the fluidization gas line 9 and the interior of the reactor 20. As discussed above, a second feed injector 24 as well as a second fluidization gas line may be connected to the fluidization nozzle 8 in place of fluidization line 9 and each may extend to any desired level within the catalyst bed 25.

A catalyst nozzle 12 is shown at an angle connected at one end to the wall of the reactor shell 21 in the region above the catalyst bed 25, and isolated with nozzle cap 13. The catalyst nozzle 12 serves as the conduit through which catalyst may be loaded into or catalyst retrieved from the reactor 20 by conventional means well known in the art. The catalyst nozzle 12 may be connected using a compression fitting and line as detailed above to provide flow to both catalyst addition and retrieval hardware (not shown).

The inert gases as well as the product gas are removed from the reactor 20 through effluent product nozzle 14. Effluent product line 15 extends axially through the effluent product nozzle 14 providing a conduit for the flow of gases to other laboratory equipment (not shown). A compression fitting 16 is disposed about the exterior surface of the effluent product line 15 and seals against a seat within the outlet of the effluent product nozzle 14. A pressure tight seal is created by connecting effluent coupling 17 to the outlet of the effluent product nozzle. A product filter 18 is connected at one end of the effluent product line 15 to prevent carry over of catalyst with the gases.

To prepare the reactor 20 for commercial simulation testing of a FCCU process, the appropriate feed injector 24 is first inserted through the top head 22 and the injector coupling 3 is connected to the top head 22 to establish a fluid tight seal. The feed injection point (designated by arrow 19) is now established with respect to the bottom of the catalyst bed, designated by lower arrow 26, and thus the catalyst-to-feed contact time is established for the prescribed catalyst charge and injection rates. The reactor 20 is then charged with the desired mass of catalyst through the catalyst nozzle 12 while fluidization gas is allowed to flow through the feed line 1, and the fluidization gas lines 2 and 9 into the catalyst bed 25. This results in the desired torrodial motion of the catalyst bed 25. The reactor 20, catalyst bed 25, and fluidization gases are operated at a desired temperature via temperature control means (not shown). The temperature control means may be an external jacket type heating element or other means well known in the art. The feed may then be injected through the feed line 1 and into the interior of the reactor 20 so as to come in direct contact with the catalyst bed 25.

The center or core of the catalyst bed 25 is of lower density since it includes gas flows and vapor phase cracked products in addition to catalyst. These materials thus flow upward and almost all of the hydrocarbon vapor products escape out of the top of the catalyst bed exiting through the effluent product line 15, while the catalyst circulates primarily back down along the interior wall of the reactor. The exiting vapor phase cracked products may be further processed and analyzed via conventional laboratory equipment. To begin a series of runs with a different hydrocarbon contact time, the catalyst bed 25 is pneumatically removed from the reactor 20 via catalyst nozzle 12 to catalyst removal means (not shown) by flowing inert gas through the lower fluidization gas line 9. The feed injector 24 is then simply removed and a different injector is installed. The process described above may now be repeated.

One skilled in the art will understand that the time the hydrocarbons contact the catalyst is directly related to the distance from the top of the catalyst bed to the feed injection point. Therefore, by solely varying the location of the feed injector 24 relative to the top of the catalyst bed 25 by gauging the distance of the injector from the apex of the conical section 7 illustrated by lower arrow 26 to a new location, it is possible to systematically alter the reaction contact time.

Techniques and advantages over prior art methods and apparatus are illustrated in the following non-limiting examples:

EXAMPLE 1

To illustrate the operation, three feed injector locations were used to crack the feedstock described in Table 1 over the catalyst described in Table 2. The catalyst charge to the reactor is 9.0 gms and the cracking temperature is 990° F. (532° C.). The results are compared in Table 3 at a catalyst-to-oil ratio of 5.0 and some of the salient results are illustrated in FIGS. 2 through 6.

TABLE 1

| FEED PROPERTIES | |
| --- | --- |
| Feedstock | Feed A |
| API Gravity | 21.2 |
| Specific Gravity, 60/60° F. | 0.927 |
| Sulfur, wt % | 0.87 |
| Conradson Carbon Residue, wt % | 0.8 |
| Distillation (D 2887) wt % | ° F./° C. |
| 10 | 659/348 |
| 50 | 833/445 |
| 90 | 983/528 |

TABLE 2

CATALYST PROPERTIES

| Catalyst | Equilibrium Cat. |
|---|---|
| Total SA, m$^2$/gm | 213 |
| Zeolitic SA, m$^2$/gm | 142 |
| Matrix SA, m$^2$/gm | 71 |
| Z/M | 2.0 |
| RE$_2$O$_3$, wt % | 2.4 |
| UCS | 24.34 |
| Nickel, ppmw | 1400 |
| Vanadium, ppmw | 2500 |

TABLE 3

YIELD AT CONSTANT CAT-TO-OIL

| INJECTOR LOCATION | 1.125" FROM BOTTOM | 2.125" FROM BOTTOM | 2.625" FROM BOTTOM |
|---|---|---|---|
| Temperature, ° F. | 990 | 990 | 990 |
| Temperature, ° C. | 532 | 532 | 532 |
| 430° F.+ Conversion, wt % | 73.06 | 71.04 | 65.38 |
| Catalyst-to-Oil, wt/wt | 5.00 | 5.00 | 5.00 |
| Delta Coke, wt % | 1.10 | 0.98 | 0.93 |
| YIELDS, WT %: | | | |
| Coke | 5.48 | 4.92 | 4.67 |
| Dry Gas | 3.11 | 2.73 | 2.43 |
| Propane | 1.53 | 1.26 | 1.06 |
| Propylene | 4.44 | 4.16 | 3.65 |
| n-Butane | 1.24 | 1.06 | 0.88 |
| Isobutane | 4.50 | 3.95 | 3.40 |
| C4 Olefins | 4.81 | 4.72 | 4.41 |
| Gasoline (C5–430° F.) | 47.94 | 48.25 | 44.89 |
| LCO (430–650° F.) | 17.39 | 17.84 | 18.43 |
| 650° F.+ | 9.56 | 11.11 | 16.19 |
| TOTAL | 100.00 | 100.00 | 100.00 |

The contact time is varied by moving the feed injector axially. The injector positions noted in the Figures are measured from the reactor bottom in accordance with FIG. 1. The relative contact time for the positions are: 1.125" injector, 1.00 relative contact time; 2.125" injector, 0.60 relative contact time; and 2.625" injector, 0.36 relative contact time. A relative contact time of 1.00 normally compares to the performance of a commercial unit with a riser contact time of 3 to 4 seconds. For these data sets the catalyst charge, feed injection rate, and diluent rates are held constant.

Figure 2:
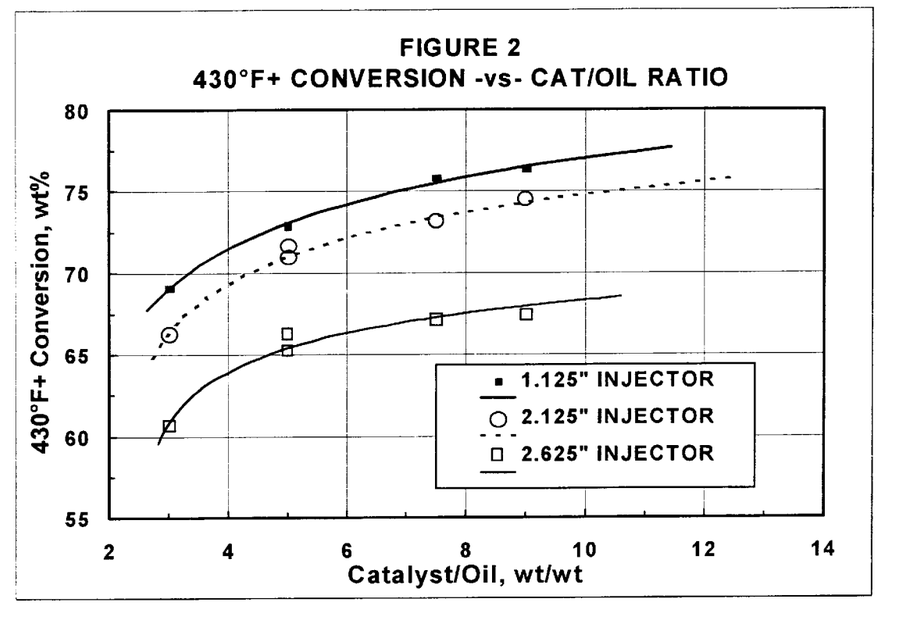
FIG. 2 is a graphical representation of 430° F.+ Conversion vs. Cat/Oil Ratio referenced in Example 1
Figure 3:
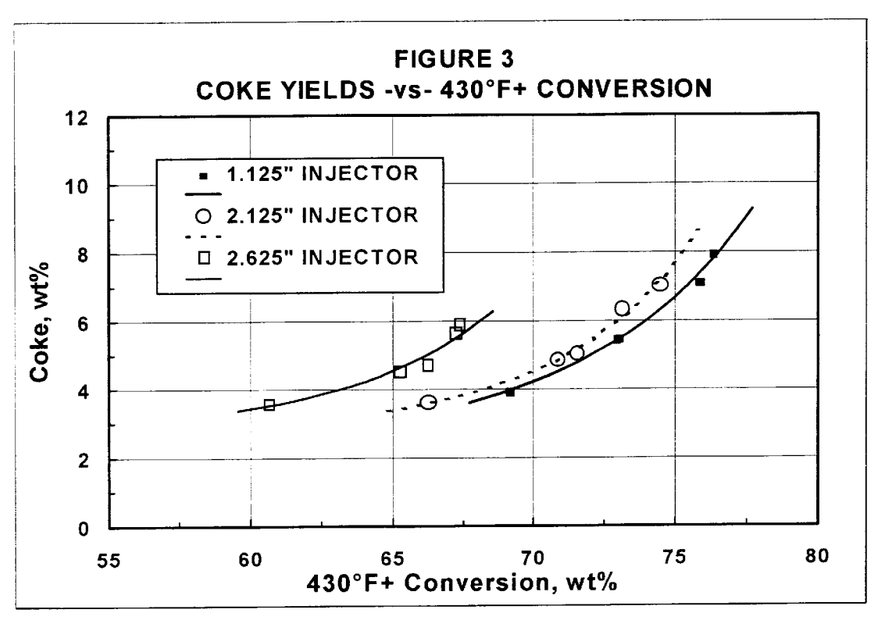
FIG. 3 is a graphical representation of Coke Yields vs. 430° F.+ Conversion referenced in Example 1
Figure 4:
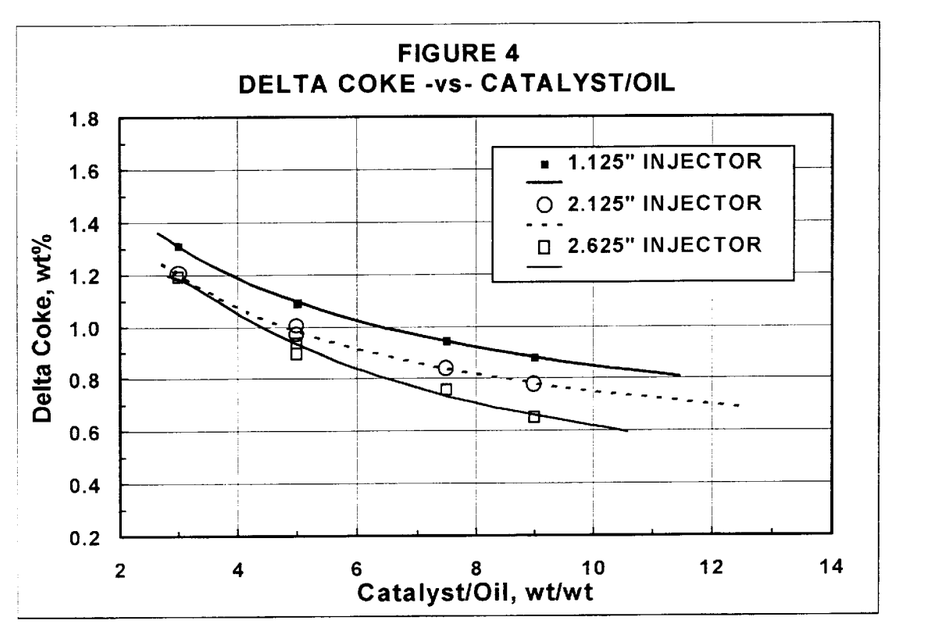
FIG. 4 is a graphical representation of Delta Coke vs. Catalyst/Oil referenced in Example 1
Figure 5:
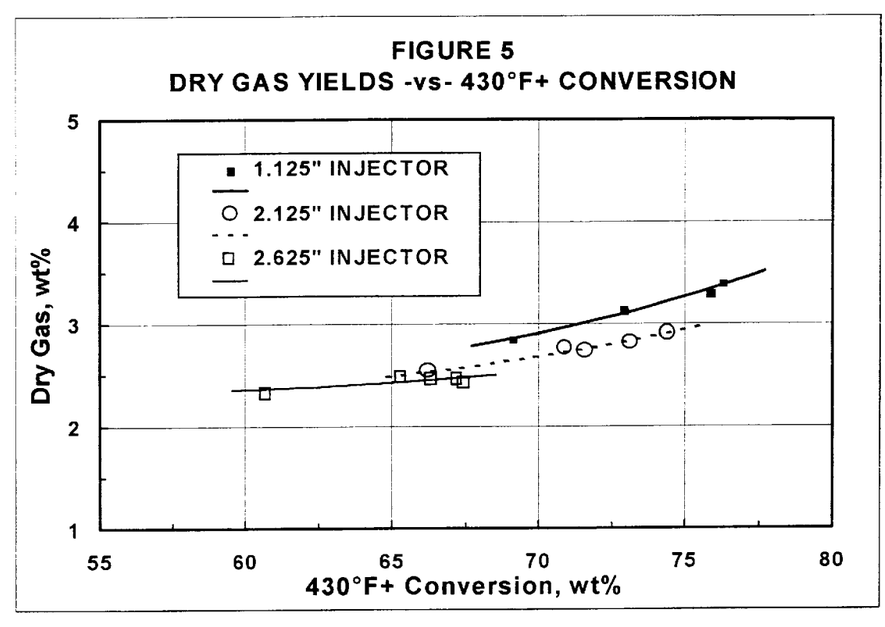
FIG. 5 is a graphical representation of Dry Gas Yields vs. 430° F.+ Conversion referenced in Example 1
Figure 6:
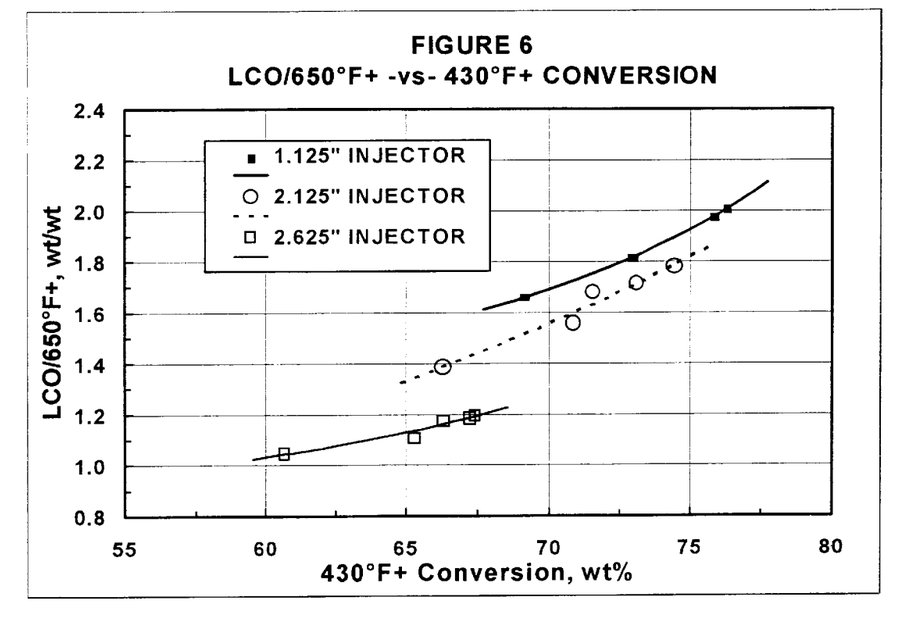
FIG. 6 is a graphical representation of LCO/650° F.+ vs. Conversion referenced in Example 1
Figure 7:
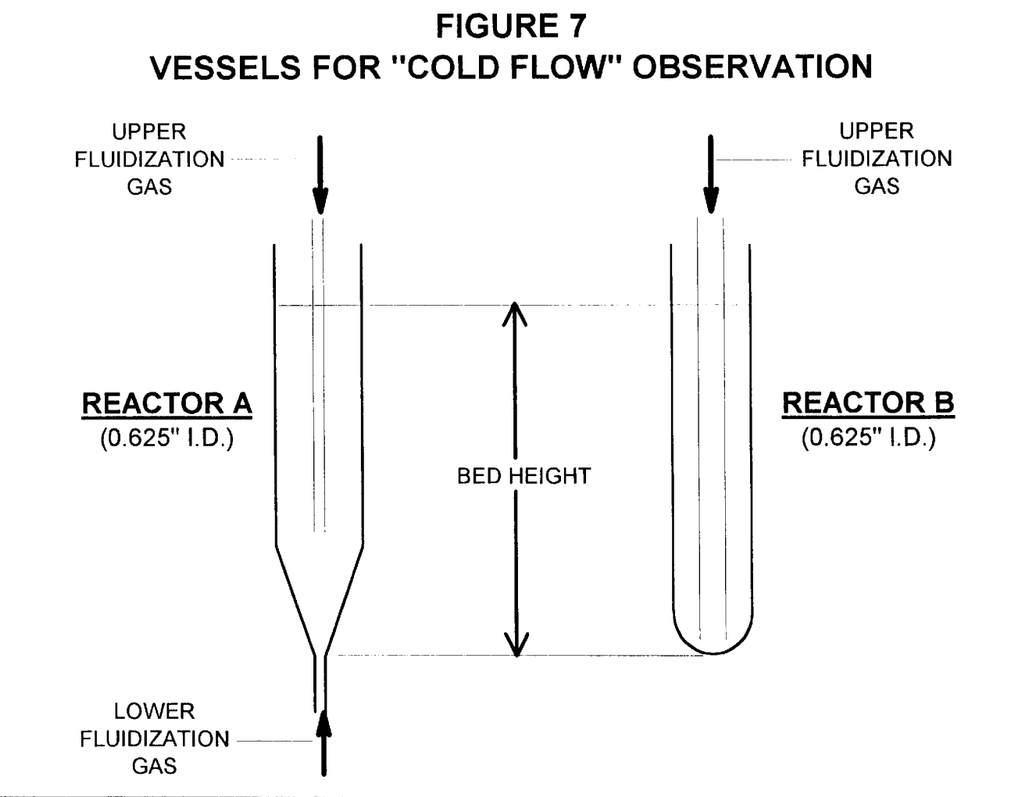
FIG. 7 is a schematic of the vessels for "Cold Flow" Observation referenced in Example 4

Decreasing contact time impacts conversion, coke, and delta coke as shown in FIGS. 2 through 4. At constant coke, as contact time decreases (going from the 1.125" injector to the 2.625" injector), conversion decreases, delta coke decreases, and required catalyst-to-oil increases. Hydrocarbon contact time influences dry gas and bottoms conversion as shown in FIGS. 5 and 6.

Table 3 shows all of the yield shifts characteristic of decreasing contact time by comparing the data at constant catalyst-to-oil. Reducing contact time of commercial operations usually increases gasoline yield. As very short contact times are employed, however, the gasoline yield begins to decrease because of conversion loss. This is effectively shown in at constant catalyst-to-oil ratio in Table 3.

EXAMPLE 2

To illustrate the relevance of the particular laboratory apparatus, data are provided in Table 4 comparing the laboratory unit to a particular commercial, full-scale fluid catalytic cracking operation with both the laboratory and commercial unit operating on the same feed and catalyst. In the table the ratio of the laboratory yields to commercial yields are indicated and the closer the values are to unity the closer is the correspondence of the performance of the lab and commercial unit.

The commercial unit is a fully modernized, short contact time unit which is operating well (with radial feed nozzles, good riser termination, and good stripper design). The operation of the Invention involved tuning the performance by moving the feed injector until the laboratory catalyst-to-oil ratio was within about 10% of the commercial catalyst-to-oil ratio (at the commercial level of conversion). The data is for a cracking temperature (initial fluid-bed) set at the commercial riser outlet temperature.

The data shows that the current invention performs within 10% of the reported commercial yields except C4 saturates. These offsets are simple to tune or further calibrate for by adjusting cracking temperature closer to the average temperature of the commercial riser. Overall, the comparison shows the invention provides data very close to commercial operation for modern fluid catalytic cracking units.

TABLE 4

COMPARISON OF LABORATORY TO COMMERCIAL DATA AT CONSTANT CONVERSION

| Parameter | Laboratory/Commercial Ratio |
|---|---|
| Cat/Oil | 0.88 |
| Coke | 1.08 |
| Dry Gas | 1.05 |
| LPG | 1.07 |
| Propane | 1.04 |
| Propylene | 1.08 |
| C4 Saturates | 1.25 |
| C4 Olefins | 0.92 |
| Gasoline | 0.96 |
| LCO | 0.96 |
| Bottoms (650° F.+) | 1.04 |
| C3 Saturation | 0.97 |
| C4 Saturation | 1.17 |

EXAMPLE 3

To illustrate the precision of the laboratory apparatus, which is a direct measure of the stability and repeatability of the fluidized bed, yield data for repeated runs are provided in Table 5. These data are with the same feed and catalyst described in Tables 1 and 2 and a temperature of 990° F. (532° C.).

The relative error values of Table 5 indicate the invention and associated analytical equipment are very precise. The relative error is nominally 2% or less for each yield. Since the analytical equipment used for these measurements are no more precise that the data itself, it is clear that the invention provides extremely reproducible performance. This is an indication of the stability of both the catalyst and feed contacting and the catalyst circulation—issues discussed further in Example 4.

TABLE 5

RESULTS FROM REPEAT RUNS AT 5 C/O

| | CRACKING DATA SUMMARY | | | | STATISTICAL SUMMARY | | |
|---|---|---|---|---|---|---|---|
| Run No. | 42 | 46 | 65 | 69 | MEAN VALUE | STD. DEV. | REL ERR. (%) |
| Date | 11/8/96 | 11/8/96 | 11/26/96 | 11/26/96 | | | |
| Recovery, wt % | 99.2 | 99.5 | 98.4 | 99.3 | 99.1 | 0.5 | 0.5 |
| Cet-to-Oil, wt/wt | 5.00 | 5.00 | 5.00 | 5.00 | 5.00 | — | — |
| 430° F.+ Conv., wt % | 72.96 | 72.93 | 73.01 | 72.67 | 72.89 | 0.15 | 0.2 |
| YIELDS, wt % | | | | | | | |
| Coke | 5.48 | 5.45 | 5.60 | 5.45 | 5.49 | 0.08 | 1.4 |
| Dry Gas | 3.11 | 3.13 | 3.08 | 3.07 | 3.10 | 0.03 | 0.9 |
| Hydrogen | 0.10 | 0.11 | 0.09 | 0.10 | 0.10 | 0.01 | 5.5 |
| $H_2S$ | 0.46 | 0.46 | 0.46 | 0.46 | 0.46 | 0.00 | 0.00 |
| Methane | 1.11 | 1.11 | 1.08 | 1.06 | 1.09 | 0.03 | 2.4 |
| Ethane | 0.69 | 0.69 | 0.70 | 0.70 | 0.69 | 0.00 | 0.4 |
| Ethylene | 0.76 | 0.76 | 0.75 | 0.76 | 0.75 | 0.01 | 0.8 |
| Propane | 1.59 | 1.50 | 1.60 | 1.52 | 1.55 | 0.05 | 1.1 |
| Propylene | 4.51 | 4.43 | 4.44 | 4.38 | 4.44 | 0.05 | 1.1 |
| n-Butane | 1.29 | 1.24 | 1.31 | 1.25 | 1.27 | 0.04 | 2.8 |
| Isobutane | 4.65 | 4.43 | 4.71 | 4.48 | 4.57 | 0.13 | 2.9 |
| C4 Olefins | 4.76 | 4.83 | 4.67 | 4.72 | 4.75 | 0.07 | 1.4 |
| 1-Butene | 1.08 | 1.08 | 1.07 | 1.06 | 1.07 | 0.01 | 0.9 |
| Isobutylene | 1.07 | 1.11 | 1.05 | 1.07 | 1.08 | 0.02 | 2.2 |
| c-2-Butene | 1.12 | 1.13 | 1.10 | 1.11 | 1.12 | 0.02 | 1.5 |
| t-2-Butene | 1.44 | 1.47 | 1.42 | 1.43 | 1.44 | 0.02 | 1.5 |
| Butediene | 0.05 | 0.04 | 0.04 | 0.05 | 0.05 | 0.004 | 7.7 |
| Gasoline | 47.57 | 47.92 | 47.59 | 47.81 | 47.72 | 0.17 | 0.4 |
| LCO | 17.43 | 17.45 | 17.49 | 17.51 | 17.47 | 0.04 | 0.2 |
| 650° F.+ | 9.61 | 9.62 | 9.50 | 9.81 | 9.64 | 0.13 | 1.3 |
| TOTAL | 100.00 | 100.00 | 100.00 | 100.00 | | | |

EXAMPLE 4

To develop the basic design of the invention of FIG. 1, a cold flow (room temperature), glass model was constructed and various reactor configurations tried. By observing and photographing the catalyst and gas interaction, the geometry and gas rates are optimized to provide the stable fluidized bed which provides the results of Examples 1 through 3. Notes from the comparison of the reactor configurations of FIG. 2 are provided in Table 6.

For the cold flow studies of this example, the superficial velocity is varied by increasing the upper fluidization flow rate to both reactors of FIG. 2. For Reactor A the lower fluidization flow is set at 180 sccm and held constant and the feed injector is 1.125 inches from the reactor bottom. The injector diameter is 0.125 inches for Reactor A and 0.250 inches for Reactor B.

The comments in Table 6 may be summarized as follows (with due qualification for the catalyst material studied): Reactor A (invention) maintains a very stable fluidized bed up to 0.50 ft/sec and the stability begins to deteriorate at velocities where solids entrainment becomes a factor. Reactor B (and many other designs) begins to slug (as large bubbles form) at superficial velocities as low as 0.15 to 0.25 ft/sec. Reactor A provides stable fluidization over a superficial velocity range that is about twice that of Reactor B. The catalyst circulates within Reactor A several times per minute as noted in Case 5 of Table 6 (at 0.35 ft/sec superficial gas velocity).

TABLE 6

VISUAL COMPARISON OF REACTOR CONFIGURATIONS OF FIG. 7

| | | Bed Height, cm Reactor | | |
|---|---|---|---|---|
| Case | Superficial Velocity | A | B | Comments |
| 1 | 0.00 cm/sec 0.00 ft/sec | 6.0 | 6.0 | Catalyst charge to each vessel is 9.0 grams of an equilibrium FCC catalyst with 0.82 gms/cc apparent bulk density. Average particle size of 79 microns |
| 2 | 1.52 cm/sec 0.55 ft/sec | 8.0 | 8.0 | Catalyst is fluidized. Reactor A is circulating even at this low velocity. There are catalyst dead zones at the bottom of Reactor B. |
| 3 | 4.57 cm/sec 0.15 ft/sec | 8.5 | 8.5 | Some large bubbles are forming in Reactor B. Reactor A remains very stable. catalyst circulation is several times faster in Reactor A than in Reactor B. |

TABLE 6-continued

VISUAL COMPARISON OF REACTOR CONFIGURATIONS OF FIG. 7

| Case | Superficial Velocity | Bed Height, cm Reactor | | Comments |
|---|---|---|---|---|
| | | A | B | |
| 4 | 7.62 cm/sec 0.25 ft/sec | 8.7 | 8.5 | Reactor A is stable with apparently no large bubbles. Slugging is severe in Reactor B. Slugging makes measuring bed height difficult (value is an average). |
| 5 | 10.7 cm/sec 0.35 ft/sec | 9.0 | 9.0 | Reactor A is still a dense bed. Catalyst circulates several times per minute. Reacotr B experiences extreme slugging with ver large bubbles. |
| 6 | 18.2 cm/sec 0.50 ft/sec | 9.0 | 9.0 | Reactor A is still a dense bed along the walls. There is more bubble aggregation and slight slugging at the top. Reactor B is extremeely turbulent/incoherent |
| 7 | 21.2 cm/sec 0.70 ft/sec | — | — | At this velocity catalyst is entrained from both reactor designs. There is a dense catalyst phase in the lower 5 cm of Reactor A but catalyst is being entrained. |

The axial injector in Reactor A was also moved in a series of flow studies. As the injector is lowered into the conical bottom the catalyst circulation pattern deteriorates and more gas bubbles and slugging occur. Apparently, the catalyst circulation pattern is more stable with the injector above the conical bottom section. As the injector is elevated above the conical section the fluidization pattern remains stable and circulates with the toroidal motion shown in FIG. 1 at all higher levels.

Since the axial position of the injector is directly related to contact time, it is clearly possible to supply one feed at one location and a second feed at another. In this way, the apparatus could be used to perform studies at multiple feed locations pertinent to commercial catalytic cracking operations.

Moreover, while the particular embodiment of the invention has been shown specific to fluid catalytic cracking, modifications or application of the invention to other catalytic processes by someone skilled in the art of reactor design are within the spirit and scope of the invention. Since the laboratory apparatus works well at emulating continuous, short contact time fluid catalytic cracking operations, it will work well in other applications. For example, partial oxidation reactions like ethylene to ethylene oxide, and isomerization reactions could be performed in the type of fluid bed shown in FIG. 1. In addition, there are many fluidized bed applications that may benefit from the invention where the solid is not strictly catalyst, the mobile phase is not strictly gaseous, and the process may not involve chemical reaction. Use of the invention in these applications is also considered within the spirit and scope of the invention.

In addition, also within the spirit and scope of the invention is continuous fluidized bed processing. Clearly, it is straightforward to apply the batch-wise concepts of this invention to fluid bed reactors operating in a continuous mode.

Near plug flow performance in the central core of the reactor with both excellent reproducibility and excellent heat transfer along the reactor wall is clearly achieved when the catalyst circulation pattern is enhanced by proper combination of geometry, gas flow rates, and injector location.

While the invention has been described in detail and with reference to specific embodiments thereof, it will be apparent to one skilled in the art that various changes and modifications can be made therein without departing from the spirit and scope thereof. It is to be understood that all matter herein set forth or shown in the accompanying tables and figures is to be interpreted as illustrative and not in a limiting sense. Accordingly, the foregoing description should be regarded as illustrative of the invention whose full scope is measured by the following claims.

What is claimed is:

1. A method for studying the effects of commercial fluidized bed processes in a laboratory fluidized bed apparatus, said method comprising:

providing a reactor having a top head and a bottom conical head;

charging said reactor with a mass of solid material to form a material bed within the reactor;

providing a source of heat for maintaining said reactor and said material bed at a predetermined temperature;

providing at least two axial injectors positioned to enhance circulation of the material bed;

wherein said at least two axial injectors comprise:
 a first feed injector disposed at the top head and comprising an upper fluidization gas line in the form of an outer tubular member and a feed line connected to the outer tubular member and extending axially therethrough, and
 a second feed injector disposed at the bottom conical head to introduce fluid to the material bed;

positioning the at least two axial injectors to predetermined axial positions within the material bed; and introducing fluid through said at least two axial feed injectors into the material bed, wherein at least one of the injectors is a removable injector axially extending through the associated head to introduce fluid at variable locations within the material bed.

2. The method of claim 1, wherein the reactor further comprises:

a catalyst nozzle for delivering a catalyst to and retrieving catalyst from the reactor; and an effluent product nozzle for transmitting product gases from the reactor.

3. The method of claim 2, wherein said effluent product nozzle includes an effluent product line having a filter connected at one end extending axially therethrough.

4. The method of claim 2, further including the steps of:
flowing inert gas through said lower fluidization gas line; and
flowing inert gas through said upper fluidization gas line.

5. The method of claim 1, wherein said fluid comprises hydrocarbon.

6. The method of claim 1, wherein the total included angle of said conical section is in the range of 10° to 170°.

7. The method of claim 1, wherein the total included angle of said conical section is in the range of 20° to 60°.

8. A versatile fluidized bed reactor comprising:
a reactor having a shell, a top head, and a bottom head and containing a catalyst bed therein;
at least two axial injectors positioned to enhance circulation of the fluidized bed;
wherein said at least two axial injectors comprise:
a first injector disposed at the top head and comprising an upper fluidization gas line in the form of an outer tubular member and a feed line connected to the outer tubular member and extending axially therethrough to introduce fluid to the catalyst bed, and
a second injector disposed at the bottom head to introduce fluid to the catalyst bed; and
wherein at least one of the injectors is a removable injector axially extending through the associated head to introduce fluid at variable locations within the catalyst bed.

9. The apparatus of claim 8, wherein said bottom head comprises a conical bottom head having a conical section to receive the second injector and a fluidization gas nozzle positioned at the apex of said conical section.

10. The apparatus of claim 9, wherein the total included angle of said conical section is in the range of 10° to 170°.

11. The apparatus of claim 9, wherein the total included angle of said conical section is in the range of 20° to 60°.

12. The apparatus of claim 9, wherein the reactor further comprises:
a catalyst nozzle extending through the reactor shell for delivering the catalyst to and retrieving catalyst from the reactor;
an effluent product nozzle for transmitting product gasses from the reactor.

13. The apparatus of claim 12, wherein said effluent product nozzle includes an effluent product line having a filter connected at one end extending axially therethrough.

14. The apparatus of claim 13, wherein the total included angle of said conical section is in the range of 10° to 170°.

15. The apparatus of claim 13, wherein the total included angle of said conical section is in the range of 20° to 60°.

* * * * *